United States Patent
Macht

(10) Patent No.: US 10,779,751 B2
(45) Date of Patent: Sep. 22, 2020

(54) SYSTEM AND PROCESS OF UTILIZING IMAGE DATA TO PLACE A MEMBER

(71) Applicant: Medtronic Navigation, Inc., Louisville, CO (US)

(72) Inventor: David E. Macht, Littleton, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 387 days.

(21) Appl. No.: 13/750,550

(22) Filed: Jan. 25, 2013

(65) Prior Publication Data

US 2014/0213889 A1    Jul. 31, 2014

(51) Int. Cl.
| | |
|---|---|
| *A61B 5/06* | (2006.01) |
| *G06T 7/00* | (2017.01) |
| *G06T 3/40* | (2006.01) |
| *A61B 6/12* | (2006.01) |
| *A61B 6/00* | (2006.01) |
| *A61B 5/00* | (2006.01) |
| *A61B 34/10* | (2016.01) |
| *A61B 17/56* | (2006.01) |
| *A61F 7/02* | (2006.01) |
| *A61F 2/00* | (2006.01) |

(Continued)

(52) U.S. Cl.
CPC ............ *A61B 5/061* (2013.01); *A61B 5/4851* (2013.01); *A61B 6/12* (2013.01); *A61B 6/486* (2013.01); *A61B 6/505* (2013.01); *A61B 34/10* (2016.02); *G06T 3/403* (2013.01); *G06T 7/0012* (2013.01); *A61B 6/485* (2013.01); *A61B 17/56* (2013.01); *A61B 2034/105* (2016.02); *A61B 2034/2055* (2016.02); *A61B 2034/2068* (2016.02); *A61B 2090/3762* (2016.02); *A61F 2/00* (2013.01); *A61F 7/02* (2013.01)

(58) Field of Classification Search
CPC . A61B 5/061; A61B 34/10; A61B 2090/3762; A61B 2034/105; A61B 2034/2068; A61B 2034/2055; A61B 6/486; A61B 6/505; A61B 6/12; A61B 6/485; A61B 17/56; G06T 3/403; G06T 7/0012
USPC ........................................................ 600/424
See application file for complete search history.

(56) References Cited

U.S. PATENT DOCUMENTS

| | | | |
|---|---|---|---|
| 6,322,565 B1 | 11/2001 | Garner et al. | |
| 6,674,883 B1 | 1/2004 | Wei et al. | |

(Continued)

FOREIGN PATENT DOCUMENTS

| | | |
|---|---|---|
| CN | 102647962 A | 8/2012 |
| EP | 2505165 A1 | 10/2012 |

(Continued)

OTHER PUBLICATIONS

Babisch, et al. "The rationale for tilt-adjusted acetabular cup navigation." J Bone Joint Surg AM, Feb. 2008, 357-365.

(Continued)

*Primary Examiner* — Amanda Lauritzen Moher
(74) *Attorney, Agent, or Firm* — Harness Dickey

(57) ABSTRACT

Disclosed is a system for acquiring and using image data and generating a three-dimensional reconstruction of a subject. The three-dimensional reconstruction can be used to assist in determining various features, including axis and planes of a subject or members placed relative to the subject. The system can be implemented to plan and perform a procedure relative to the subject.

17 Claims, 5 Drawing Sheets

(51) Int. Cl.
   *A61B 34/20*     (2016.01)
   *A61B 90/00*     (2016.01)

(56) References Cited

U.S. PATENT DOCUMENTS

| | | | |
|---|---|---|---|
| 7,764,985 B2 | 7/2010 | McCombs et al. | |
| 8,233,963 B2 | 7/2012 | Hartmann et al. | |
| 8,239,001 B2 | 8/2012 | Verard et al. | |
| 8,271,069 B2 | 9/2012 | Jascob et al. | |
| 8,308,361 B2 | 11/2012 | Gregerson et al. | |
| 8,320,991 B2 | 11/2012 | Jascob et al. | |
| 8,325,873 B2 | 12/2012 | Helm et al. | |
| 8,861,818 B2 | 10/2014 | Ito et al. | |
| 2003/0153829 A1 | 8/2003 | Sarin et al. | |
| 2003/0176860 A1 | 9/2003 | Shimura | |
| 2003/0194057 A1* | 10/2003 | Dewaele | G06T 7/0012 378/210 |
| 2004/0133276 A1* | 7/2004 | Lang | A61F 2/30756 623/14.12 |
| 2005/0065617 A1 | 3/2005 | Moctezuma de la Barrera et al. | |
| 2006/0293614 A1* | 12/2006 | Radinsky et al. | 600/587 |
| 2008/0287781 A1* | 11/2008 | Revie et al. | 600/426 |
| 2009/0198276 A1* | 8/2009 | Lee | 606/237 |
| 2010/0030231 A1* | 2/2010 | Revie | A61B 90/36 606/130 |
| 2011/0313424 A1* | 12/2011 | Bono et al. | 606/91 |
| 2012/0230573 A1 | 9/2012 | Ito et al. | |
| 2013/0072821 A1* | 3/2013 | Odermatt | A61B 5/06 600/595 |
| 2014/0093154 A1* | 4/2014 | Penenberg | 382/132 |

FOREIGN PATENT DOCUMENTS

| | | | |
|---|---|---|---|
| JP | 2002159478 A | 6/2002 | |
| JP | 2003-271749 A | 9/2003 | |
| JP | 2008-534208 A | 8/2008 | |
| WO | WO-2006079211 A1 | 8/2006 | |
| WO | WO-2006/109022 A2 | 10/2006 | |
| WO | WO-2011/065378 A1 | 6/2011 | |

OTHER PUBLICATIONS

Dikmen, et al., "Joint Detection and Localization of Multiple Anatomical Landmarks Through Learning", Medical Imaging 2008, Computer Aided Diagnosis, vol. 6915, 691538, (2008).

Murray, D.W. "The Definition and Measurement of Acetabular Orientation," J Bone Joint Surg AM, 1993, 228-232.

International Search Report and Written Opinion dated Jun. 6, 2014 for PCT/US2014/012958 claiming benefit of U.S. Appl. No. 13/750,550, filed Jan. 25, 2013.

International Preliminary Report on Patentability and Written Opinion dated Aug. 6, 2015 for PCT/US2014/012958 claiming benefit of U.S. Appl. No. 13/750,550, filed Jan. 25, 2013.

Japanese Office Action for JP Application No. 2015-555344 dated Oct. 21, 2016 corresponding to PCT/2014/012958 which claims benefit of U.S. Appl. No. 13/750,550, filed Jan. 25, 2013.

Chinese Office Action dated Jul. 10, 2018 in corresponding Chinese Application No. 2014800005976.6.

Japanese Office Action for JP Application No. 2017-184401, dated Oct. 2, 2019.

Office Action dated Jan. 11, 2019 in corresponding Chinese Application No. 201480005976.6.

Office Action dated Mar. 14, 2019 in corresponding Japanese Application No. 2017-184401.

Office Action regarding Canadian Patent Application No. 2,898,634, dated Jan. 7, 2020.

Japanese Office Action for JP Application No. 2015-555344 dated May 26, 2017 corresponding to PCT/2014/012958 which claims benefit of U.S. Appl. No. 13/750,550, filed Jan. 25, 2013.

Australian Office Action dated Aug. 25, 2017 for Australian Application No. 2014209244 corresponding to PCT/2014/012958 which claims benefit of U.S. Appl. No. 13/750,550, filed Jan. 25, 2013.

Japanese Office Action dated Jun. 14, 2018 in corresponding Japanese Application No. 14752477.1.

Chinese Office Action for CN Application No. 201480005976.6 dated Mar. 17, 2017 corresponding to PCT/2014/012958 which claims benefit of U.S. Appl. No. 13/750,550, filed Jan. 25, 2013.

European Office Action for EP Application No. 14708127.7 dated Mar. 20, 2017 corresponding to PCT/2014/012958 which claims benefit of U.S. Appl. No. 13/750,550, filed Jan. 25, 2013.

European Office Action dated Jan. 18, 2018 in corresponding European Application No. 14708127.7.

* cited by examiner

SYSTEM AND PROCESS OF UTILIZING IMAGE DATA TO PLACE A MEMBER

FIELD

The subject disclosure is related to a system and process of utilizing image data, and particularly to identifying various geometrical or structural features based upon identified landmarks in the image data.

BACKGROUND

This section provides background information related to the present disclosure which is not necessarily prior art.

An image can be acquired of the subject for various purposes. For example, an image can be acquired of a human patient for assisting in planning and/or performing a procedure on a patient. A surgical procedure can include a hip joint replacement. In replacing a hip joint, a femoral head and an acetabular cup can be placed in the patient to replace the natural femoral head and acetabulum that may be removed due to injury or other reasons. To assist in performing a procedure, images can be acquired of the subject such as prior to removing the femoral head or acetabulum or following removal and during a trialing procedure. Additionally, images can be acquired of the subject to assist in confirming proper placement of the prosthetic members.

SUMMARY

This section provides a general summary of the disclosure, and is not a comprehensive disclosure of its full scope or all of its features.

During a procedure on a patient, or any other procedure on a subject, images can be acquired of the patient. The images of the subject can include landmarks of the subject. Landmarks of the subject can include landmarks of boney regions of a human patient. The boney regions can be identified in the image data to assist in identifying a geometry (also referred to as a geometric configuration) of the patient for assisting in performing and completing a surgical procedure. For example, boney landmarks can be identified in x-ray images of a subject to identify at least one plane relative to a pelvis for placement of an acetabular cup. The geometry of the subject can assist in achieving a selected range of motion of a femur, a leg length, a version, and other selected results of an acetabular and femoral head placement.

A geometry (also referred to as a geometrical configuration) of a prosthetic system can be determined. For example, a prosthesis or trial prosthesis can be positioned relative to the subject. The image data can include images of the prosthesis as well. Thus, the geometry of the prosthesis can be determined. The geometry of the prosthesis can then be evaluated and illustrated relative to the subject geometry.

Image data can be acquired of the patient through various techniques, such as acquiring a plurality of projections and generating a three-dimensional reconstruction thereof. The three-dimensional reconstruction can be used to assist in determining various anatomical features, including a plane of the acetabulum, a position of the femoral head, and other selected anatomical features.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

In a procedure on a subject, such as an operative procedure on a patient, a device can be positioned in a patient. The device positioned in the patient can be an implantable device that is implanted into the patient or positioned in the patient only for providing a therapy. Exemplary implantable devices include prosthetic devices which can include systems of more than one member. Prosthetic systems can include a femoral hip prosthesis, an acetabular prosthesis, or other joint prosthetics. Other implantable devices can include implants to replace portions of a spinal column. Still further implantable devices can include implantable cardiac devices (ICD), such as pacing or monitoring devices. Therapeutic devices can be provided, such as an ablation catheter for ablating tissue during an operative procedure, but is not permanently implanted.

Figure 1:
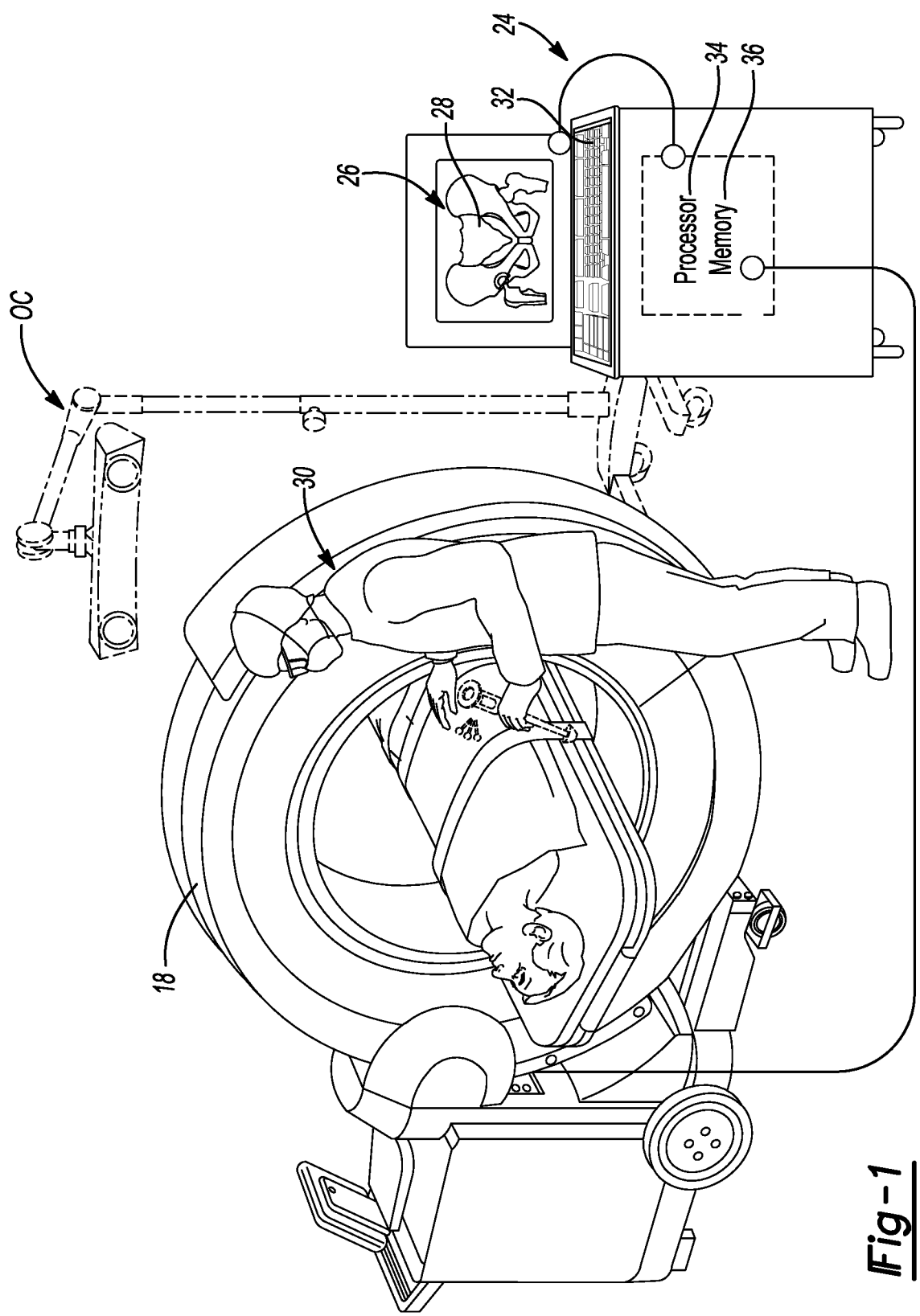
FIG. 1 is an environmental view of a subject positioned relative to an imaging system.

With various systems, the device can be navigated to a selected location with a navigation system that includes a tracking localizer OC, as illustrated in FIG. 1. Exemplary surgical navigation systems include a StealthStation® S7® surgical navigation system, a StealthStation® i7® surgical navigation system, a StealthStation® AxiEM™ surgical navigation systems, and other surgical navigation systems sold by Medtronic Navigation, Inc. having a place of business in Colorado. Exemplary navigation systems are also disclosed in U.S. Pat. Nos. 8,320,991; 8,271,069; 8,239,001; and 8,233,963, all incorporated by reference. The navigation systems can be used to determine the location of a tracking device. The tracking device can be associated with an instrument during an operative procedure. The location of the tracking device can be registered to an image of the subject to identify and/or illustrate a location of the instrument relative to the image data of the subject on a display device.

The various embodiments of navigation systems may be used to perform a procedure or assist in guiding an instrument during a procedure. The implementation may include placing a dynamic reference frame (DRF) on a subject or fixing of the subject relative to a navigation field. The use of the navigation system may include preparing the subject for the procedure by acquiring appropriate image data, preparing the subject by positioning the tracking devices on the subject, and preparing using appropriate navigable instruments.

In addition, to the navigation system, an imaging system 18 can be provided to image a subject at a selected time. The subject can be imaged prior to procedure, during a procedure, and following a procedure. The image data and the related images of the subject can be used to assist in performing a procedure and/or confirming that a procedure has been performed properly or according to a pre-selected configuration or plan. Various imaging systems can include the O-Arm® medical imaging device, sold by Medtronic Navigation, Inc. having a place of business in Louisville, Colo. The O-Arm® imaging device can acquire image data of a subject at positions substantially 360° around the subject. Additionally, image data can be acquired by imaging systems such as that disclosed in U.S. Pat. Nos. 8,308, 361 and 8,325,873, all incorporated herein by reference. Accordingly, the O-Arm® imaging device can be used to form a three-dimensional reconstruction of an image of the subject based on a plurality of two-dimensional projections of the subject. The image data acquired of a patient in a selected manner can be used to assist in viewing various portions of the patient, such as internal portions that are not open during a surgical procedure. It is understood, however, that other imaging systems can be used, such as a computed tomography imaging system, an MRI imaging system, a C-Arm or other configuration of fluoroscope, as is generally known in the art.

Based upon image data, various portions of an anatomy can be identified. For example, anatomical landmarks can be identified in image data using various landmark identification techniques. Landmark identification techniques can include identifying landmarks in image data, such as by segmentation, that are performed a processor system 24. Various landmark identification techniques are also disclosed in Dikmen, et al., "Joint Detection And Localization Of Multiple Anatomical Landmarks Through Learning", Medical Imaging 2008, Computer Aided Diagnosis, Vol. 6915, 691538, (2008), by incorporated herein by reference. Identification of landmarks in image data can assist in identifying the location of planes, locations, etc. in the image data. The landmarks, as discussed in Dickmen, et al., can be identified using a plurality of classification techniques to assist in identifying selected landmarks.

In addition, a user 30 can identify land marks in the image data. As discussed herein, a selected number of the landmarks can then be used to determine planes and other subject geometric configurations. The determination of at least a portion of the geometric configuration can be performed substantially automatically using a processor system 24, as discussed herein.

Further landmark and/or geometric configuration determination techniques can include atlas model matching. For example, an atlas model of a "standard" or phantom subject can have predefined landmarks and planes thereon. The atlas can then be matched to a specific subject, such as by morphing. The atlas model can be stored in a memory system and the morphing and matching can be performed using generally known techniques executed by the processor system. Once the matching has occurred then landmarks and planes can be identified in the specific subject for a procedure.

Accordingly, identifying landmarks in image data can be performed once image data is acquired and/or accessed of the subject. The identification of landmarks can be performed by a processor system, as discussed herein, executing an algorithm based on the instructions to identify landmarks as noted above. For example, generally known anatomical landmarks can be used to identify selected planes, axes, and points of the anatomy to defined portions of the anatomy.

In various procedures on a subject, an internal view of a subject may be desirable. An internal view of a subject may be desirable for performing a selected procedure on the subject, such as a surgical procedure including a total hip arthroplasty (THA). Other surgical procedures can include pelvic osteotomies, revision procedures (such as proximal femoral revisions, distal femoral revisions, and acetabular revisions), resurfacing procedures, total shoulder replacements, bone reduction in trauma cases, and other selected surgical procedures. Also, image data can be acquired for performing various "soft" tissue procedures such as heart lead placement and deep brain lead placement.

Figure 3A:
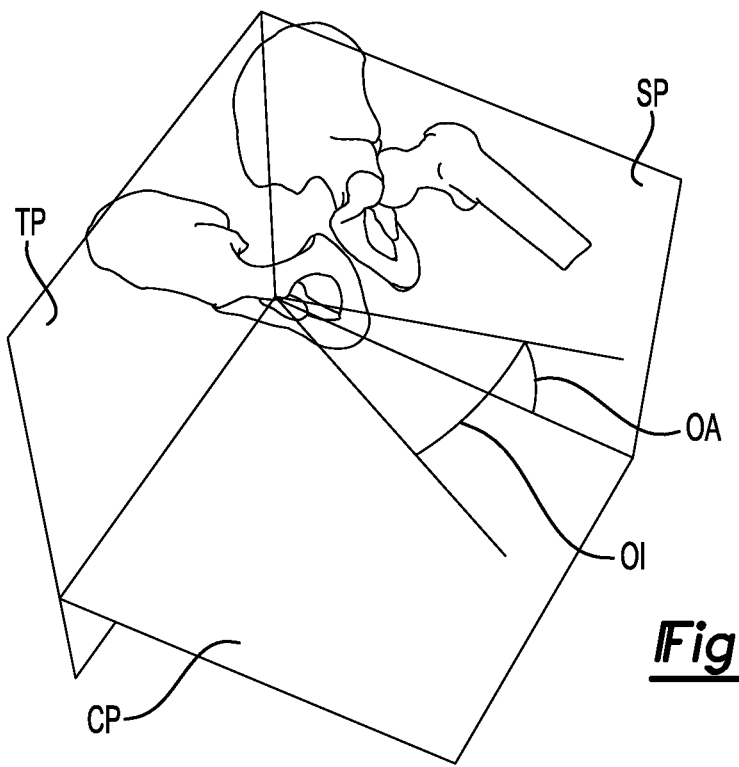
FIGS. 3A-3C illustrate exemplary measurement calculations.
Figure 3B:
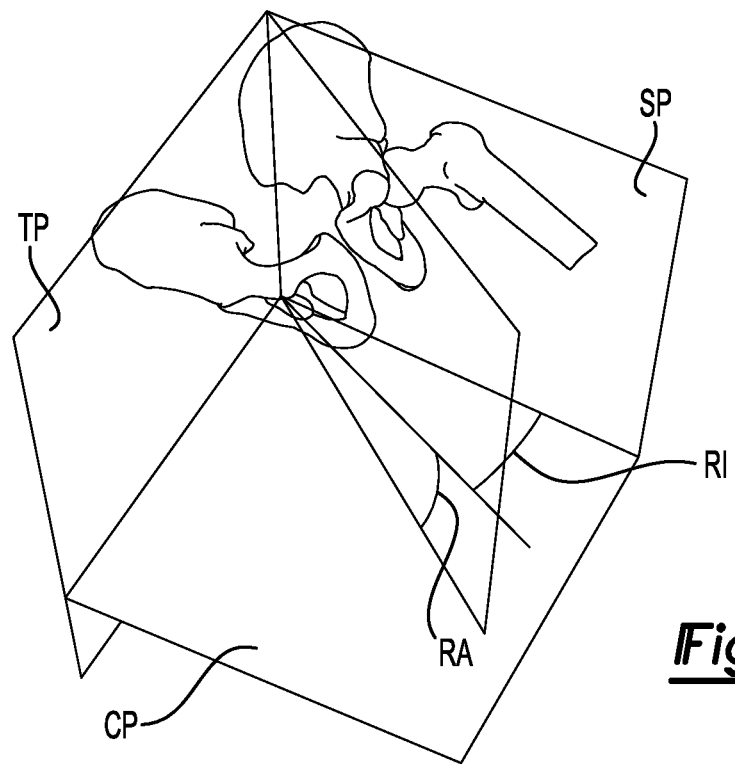
Figure 3C:
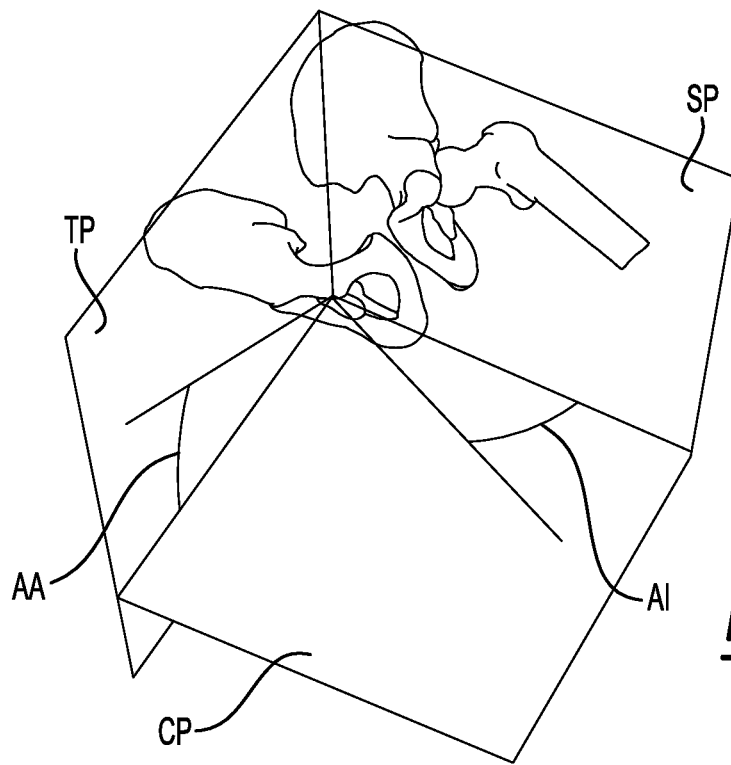

The surgical procedures can be assisted with imaging procedures and processes, as discussed further herein, including those to identify various landmarks of the patient during a procedure. Identifying landmarks in the image data of the subject during a procedure can assist a user 30, such as a surgeon, in determining an appropriate placement of the prosthetic devices and confirmation of the selected placement. Additionally, analysis of images can, as illustrated in FIGS. 3A-3C, identify various planes of a patient, such as a Sagittal Plane (SP) (which can include a mid-sagittal plane), an anterior pelvic plane (APP), and a transverse plane (TP). The APP is generally parallel to a Coronal Plane of the patient 20, but may not be parallel. The APP is defined by the two ASIS points and the two tuberacles. Additional planes can include a Coronal Plane (CP) of the patient 20. The CP generally bisects the patient 20 from head-to-toe. The CP may generally be parallel to a flat table that the patient 20 is laying on, but the CP may not be parallel to the APP. The angle difference between the APP and the CP can be used to assist in identifying a selected angle for viewing by the user 30. In one example, the angle of the positioned instruments can be determined and illustrated relative to both the APP and the CP. The CP is discussed in Babisch, et al. "The rationale for tilt-adjusted acetabular cup navigation." J Bone Joint Surg AM, February 2008, 357-365, incorporated herein by reference. Other geometric configurations of the subject can also be determined such as a relative Leg-Length and Offset (LLOS) discrepancies between ipsilateral and contralateral legs, particularly during a hip procedure.

As is generally known, navigation systems, including those disclosed above, can assist in performing various procedures. The navigation systems can identify various portions of the patient, tools, and identify the relative locations thereof in the image data. The relative locations can then be viewed on a display device. The relative locations of the portions of the patient and the instruments can assist in identifying locations of the various portions to assist in determining the selected relative locations. Also, the tracked and determined relative locations can confirm selected relative locations during a procedure. If the use of surgical navigation is not indicated, desired, or performed, images can assist in identifying and confirming an appropriate procedure, planning an appropriate procedure, and enhancing workflow of a procedure.

According to various embodiments, the imaging device 18, including the O-Arm® imaging device discussed above, can acquire images of a subject 20, which can include a human patient. As an example, and discussed in detail herein, a hip arthroplasty, including a total arthroplasty, can be performed. In a total hip arthroplasty, a proximal femoral prosthesis can be positioned in a proximal femur after resection of a proximal femur portion. In the THA, an acetabular prosthesis can be positioned in an acetabulum after resection of an acetabulum. The procedure can be assisted by imaging various portions of the subject 18, including a majority of the pelvis and a proximal portion of the femur. For example, a proximal portion of the femur can be imaged during acquisition of images of the pelvis given a large enough field of view. As discussed herein, the disclosed system can be used to identify various portions of the subject 20, including the subject's anatomy, based upon the acquired images of the subject 20.

With continuing reference to FIG. 1, image data of a subject 20 can be acquired with the imaging system 18, including the O-Arm® imaging system discussed above, according to generally known techniques. The imaging system 18, can acquire the image data of the subject 20 for transmission and viewing on various systems. For example, an image viewing and manipulation system, including a processor system 24, can include a display device 26 for viewing image data or images 28 of the patient. The display device 26 can display the images 28 of the patient for viewing by a surgeon 30. The surgeon 30 can manipulate the image data or images 28 and various portions (such as identified planes and axes that can be represented by icons superimposed on the image data) relative thereto using various user input systems, such as a keyboard 32, a mouse, foot pedal, or other user input devices. Generally, the system 24, however, also includes a processor 34 and a memory system 36. The memory system 36 can store, either permanently or for a selected period of time, data and program instructions for manipulating image data. The processor 34 can execute programs stored on the memory system 36 or otherwise retrieved to identify various portions of the image data for display on the display device 26. The identified portions (such as landmarks, planes, and axes) of the images can be displayed relative to the image 28 of the patient, such as super-imposed icons thereon.

The system 24, which can be separate or integrated into the imaging system 18, can identify or reconstruct three dimensional images of the subject 20. Generally, the image system 18, including the O-Arm® imaging system discussed above, generates two-dimensional projections of the subject 20 from various directions. The plurality of two-dimensional projections can be used to generate a three-dimensional reconstruction of the subject 20, according to various techniques including those described in the patents incorporated by reference above. Generally, the three-dimensional reconstruction can be viewed by a user on the display device 26 to view the subject 20 at various perspectives and directions on the display device 26. Accordingly, the user 30 is not limited to individual two-dimensional views of the subject 20 when performing or confirming a procedure.

Additionally, the images acquired of the patient 20 can be transported physically or digitally to various systems, such as with a wireless or wired transmission system or physical media. Also, the imaging system 18 can be used to image the patient 20 in a substantially sterile manner. The imaging system 18 can include a C-Arm configuration that has a passage for the patient 20 to exit the imaging system 18. In addition, the O-Arm® imaging system can include a breakaway or movable portion to allow the patient 20 to be removed from an imaging volume of the imaging system 18.

Figure 2:
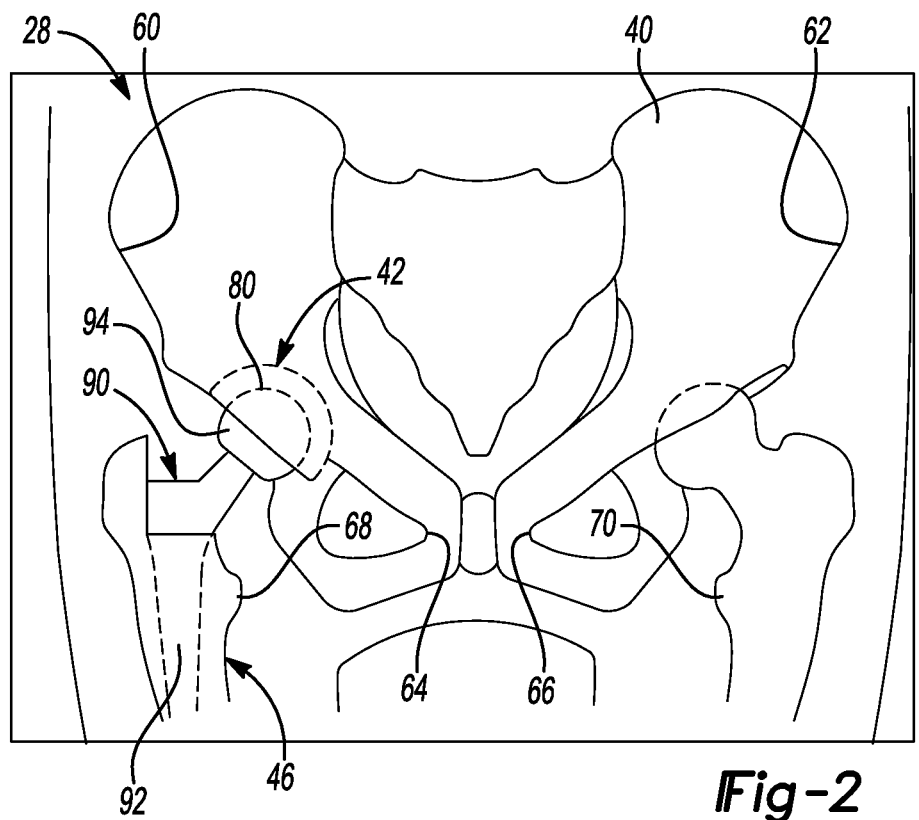
FIG. 2 is an exemplary screen shot of an image and identified landmarks.

According to various embodiments, and with continuing reference to FIG. 1 and additional reference to FIG. 2, the images 28 can include images of a pelvis 40 including an acetabulum 42 and other anatomical features of a pelvis, and a proximal femur 46. The images, as discussed herein, can also include image data regarding a positioned prosthesis system. As discussed herein, such as in relation to FIG. 6, the image data can be acquired prior to placing the prosthesis system or after placing the prosthesis system for various purposes. Thus, the image data may or may not include the prosthesis system and may or may not be used to determine a geometric configuration and relation of the prosthesis system.

Various portions of the pelvis 40 and the femur 46 can be determined and identified in the image data. For example, an ipsilateral anterior superior iliac spine (ASIS) and a contralateral ASIS can be identified in the image 28. Additional pelvic landmarks can include the pubic tuberacles on both sides of the pelvis 40. Femur landmarks can be identified including the ipsilateral lesser trochanter 68 and the contralateral lesser trochanter 70. The ipsilateral portion generally refers to that portion or the side upon which a procedure is occurring. As illustrated in FIG. 2, a right femur and right acetabulum is being replaced or has been replaced. Accordingly, in FIG. 2, the right side of the patient is the ipsilateral side and the left side is the contralateral side.

The various anatomical landmarks, including those listed above, and additional landmarks if more are selected by the user 30, can be automatically identified with the system 24 by executing various instructions with the processor 34 based upon the image data 28. The processes to identify the selected anatomical landmarks can be based upon selected methods and algorithms, including those disclosed in Dikmen et al. and others, including those discussed above. As discussed above in Dikmen et al., various landmarks of the patient in the image data can be identified using selected techniques, including a dual identification technique. The landmarks can be identified in the two dimensional and/or the three-dimensional reconstructions.

In addition, or alternatively to the automatic detection, the user 30 can assist in identifying the anatomical landmarks. For example, during a procedure, the user 30 can view the image 28 on the display device 26 and can identify the anatomical landmarks therein. The user can identify landmarks in the image data and select them with the user input 34. Also, if a tracked instrument is used, the user 30 can touch points on the patient 20 that have been registered to the image data to identify landmarks therein. The user 30 can alter or identify alternative landmarks in the image 28 based upon the user's preference, knowledge, expertise and experience, and other factors. Generally, the field of view of the imagining device 18 of the patient 20 is large enough to generate a projection or a three-dimensional reconstruction that extends from the iliac crest to past a lesser trochanter (68, 70 FIG. 5) on the femur. Generally, the image data can extend from an iliac crest of the pelvis 40 to inferior of the lesser trochanter of the femur 46. Also, the field of view can extend to image both the left acetabulum and the right acetabulum and the ipsilateral ASIS and the contralateral ASIS. Thus, the field of view of the patient can include substantially the entire pelvis of the patient 20. Generally the field of view can be about 40 centimeters (cm) to acquire adequate image data of the subject 20.

Various anatomical planes can be identified based upon the identified anatomical landmarks, discussed above in relation to FIG. 2, or based upon other identifiable and determined anatomical structures. The imaging system 18 in conjunction with or the processing system 24 alone can be used to determine the planes based on the selected landmarks. The various anatomical planes can include the planes discussed above, such as the APP, in addition to or along with a transverse plane (TP), a sagittal plane (SP), and coronal plane (CP).

Generally, a selected number of the landmarks can be used to define one of the planes or the plane relative to the landmarks. For example, the ASIS landmarks and the tuberacles (which can be an alternative to a determination and identification of only the pubic symphysis) can be used to define the APP, which may or may not be parallel with the coronal plane, as discussed above. It is understood that the landmarks can include a surface or region that is more than one discrete point. Thus, after determining the landmarks enough information is determined to define a plane. Moreover, the landmarks can be used to morph an atlas model to the image data. The atlas model may have the planes predefined therein. Thus, the planes can be predefined in the atlas and matched to the image data. Again, the determination of the planes, according to the various embodiments, can be determined with the processor system 24.

Various measurement protocols can be used to measure a prosthesis system location and orientation relative to the patient 20. Generally-known measurement protocols can include those disclosed in Murray, "The Definition and Measurement of Acetabular Orientation," J Bone Joint Surg AM, 1993, 228-232, incorporated herein by reference. For example, measurement protocols can include an operative measurement protocol, radiographic measurement protocol, and anatomical measurement protocol. As illustrated in FIGS. 3A, 3B, and 3C, the different measurement protocols can be used to identify positions of a prosthesis system, including an acetabular prosthesis 80. A femoral prosthesis may also be placed in the patient 20 and can include a stem portion 92 and a femoral head portion 94. It is understood that the prosthesis system can include a trial portion and an implantable portion. The trial portion, as understood by one skilled in the art, is placed in the patient 20 to determine proper orientation, placement etc. The trial is then removed for placement of the implantable members. It is further understood that a trial portion is not required.

According to the various measurement protocols, the plane of the anatomy of the subject 20 are the same or substantially same through all measurement protocols. However, measurements that define the location and orientation of the prosthesis system relative to the planes can vary based upon the protocols, which can be selected by a specific user based on inclination or experience. For example, with reference to FIG. 3A, in an operative measurement protocol, a position of the acetabular prosthesis 80 can be measured relative to the three planes (i.e., transverse plane, sagittal plane, and coronal plane). The measurements can include an anteversion angle and an inclination angle. The operative anteversion is an angle between the longitudinal axis of the patient and an acetabular axis (generally an axis extending from an apex of the natural acetabulum or acetabular prosthesis) projected on the sagittal plane. The operative inclination is an angle between the acetabular axis and the sagittal plane.

The radiographic measurement protocol, as illustrated in FIG. 3B, includes an anteversion angle and an inclination angle. The radiographic inclination angle is an angle between a longitudinal axis of the patient and the acetabular axis projected on the coronal plane. The radiographic anteversion angle is the angle between the acetabular axis and the coronal plane.

Finally, an anatomical measurement protocol can be used, as illustrated in FIG. 3C. The anatomical measurement protocol can include an anteversion angle and an inclination angle. The anatomic anteversion angle is an angle between a transverse axis of the patient and the acetabular axis measured on the transverse plane. The anatomic inclination angle is an angle between the acetabular axis and the longitudinal axis of the patient.

Accordingly, various measurement protocols can be used to determine the orientation and position of the acetabular prosthesis 80. The system 24 can be used to identify the various planes of the subject 20 in the image 28 for display on the display device 26. The various angles can then be determined and displayed relative to the identified planes for viewing by the user 30. The user 30 can select a measurement protocol with the user input 34, including the operative, radiographic, and anatomical, for viewing on the display device 26. Thus, the user 30 can identify the selected measurement protocol that is most appropriate or comfortable for the user 30. The user 30 need not be limited to a specific measurement technique, but rather can select during a procedure the measurement protocol desired by the user 30.

Figure 4:
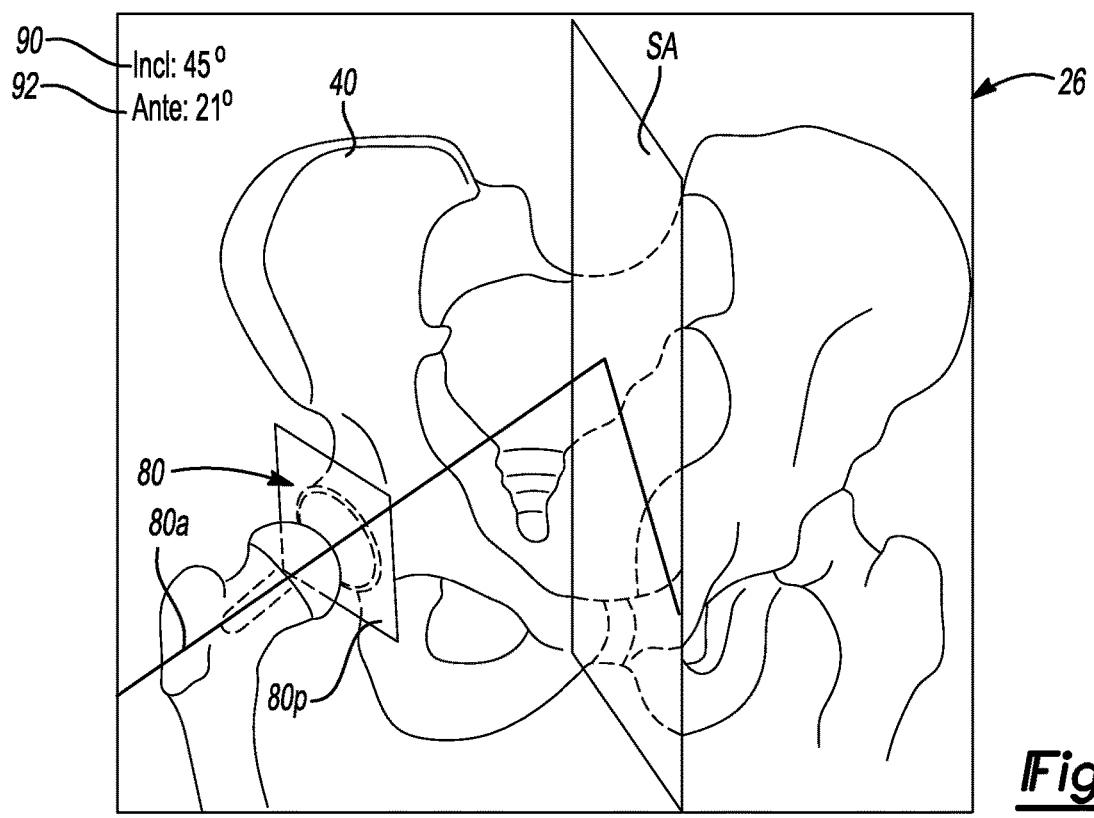
FIG. 4 is an exemplary screen shot illustrating a first geometric configuration of a subject and prosthesis.

Accordingly, with reference to FIG. 4, the display device 26 can exemplary display an orientation of the prosthetic cup 80 (or a trial cup). The system 24 can identify a face plane 80p of the cup 80 and a cup axis 80a of the cup 80. The cup 80, the face plane 80p of the cup 80, and the cup axis 80a can all be displayed alone or superimposed on image data of the patient 20. As discussed above, the image data can be direct image data (i.e. x-ray projections) or can be reconstructions (e.g. 2D or 3D) of the image projections.

The cup face plane 80p can be identified as a plane generally defined by at least three points on the upper rim of the cup 80. The three points on the upper rim of the cup can be identified by the user, such as with the user input 34 or by touching with a navigated instrument. Also, the at least three points can be automatically determined by the system 24, such as with edge detection techniques. In edge detection the processor system 24 can identify the cup 80 in the image 28 using generally known segmentation techniques that can segment the cup 80 from the other portions of the anatomy, such as those that are substantially bone portions. The at least three points on the rim of the cup 80 in the segmented image can then be identified.

The cup axis 80a is generally substantially perpendicular to the cup face plane 80p and extending through an apex of the cup 80. Using generally known geometric calculations, the cup axis 80a can also be identified. That is, a line perpendicular to the face plane 80p can be determined that extends through the apex of the cup, this line is the cup axis 80a.

As discussed above, the planes relative to the subject 20 and the various portions of the anatomy can be identified such that the orientation of the cup 80 relative to the pelvis 40 can be displayed for the user 30. According to various techniques, the inclination angle 90 and the anteversion angle 92 can be displayed on the display device 26. The various planes, such as the sagittal plane, can also be displayed. It is understood, however, that the cup-face plane 80p, the cup axis 80a, and the plane SA need not be displayed on the display device 26. In addition, the inclination angle 90 and the anteversion angle 92 can be displayed with various techniques such as in a chart, as illustrated in FIG. 4, or relative to the portions of the prosthesis 80 in the anatomy, including the pelvis 40 as illustrated in FIG. 4. The system 24 can also substantially automatically identify the inclination angle 90 and the anteversion angle 92 for viewing by the user 30 during an operative procedure.

The user 30 can also view the image data and determine implanted angles for the implanted prosthesis to assist in performing the procedure on the subject 20. For example, an implanted inclination angle 90 and an implanted anteversion angle 92 can be identified prior to performing the procedure. Then, after imaging the subject 20 with the imaging device 18 after placing the trial or the implantable prosthesis, the inclination angle 90 and the anteversion angle 92 can be determined to determine whether the prosthesis 80 is at the selected position. If the inclination angle 90 and the anteversion angle 92 are not at selected positions, the user 30 can reposition the prosthesis 80 to achieve a selected or pre-planned orientation of the prosthesis relative to planes of the subject 20.

To achieve a selected location and orientation of the prosthesis the user 30 can move the prosthesis 80 based upon experience to achieve the desired angle, if not achieved during the initial placement. In addition, or according to various embodiments, the tracking system can be used to track the prosthesis 80 or instruments used to position the prosthesis 80. Various tracking systems can include the optical tracking systems that may include the exemplary or optional optical localizer OL (shown in phantom in FIG. 1) or other tracking system, including an electromagnetic tracking system. The tracking systems include those incorporated by reference discussed above, and generally known to one skilled in the art. It is understood, however, that a tracking system or surgical navigation system with a tracking system is not necessary. In addition, alternative or subsequent imaging is not required based upon the user's 30 selection.

In addition to an orientation of the selected prosthesis, including the acetabular prosthesis discussed specifically above, other anatomical prosthesis can also be imaged, identified, and oriented with the image 28. It is understood that the acetabular prosthesis is discussed in detail above but that the femoral prosthesis 90 can also be imaged, identified, and oriented in the image 28. Other selected prostheses, including those discussed above, such as a knee prosthesis, a shoulder prosthesis, and other prosthetic devices can also be imaged and identified in the image 28 for determining and identifying orientations and positions of the prostheses relative to the subject image.

Figure 5:
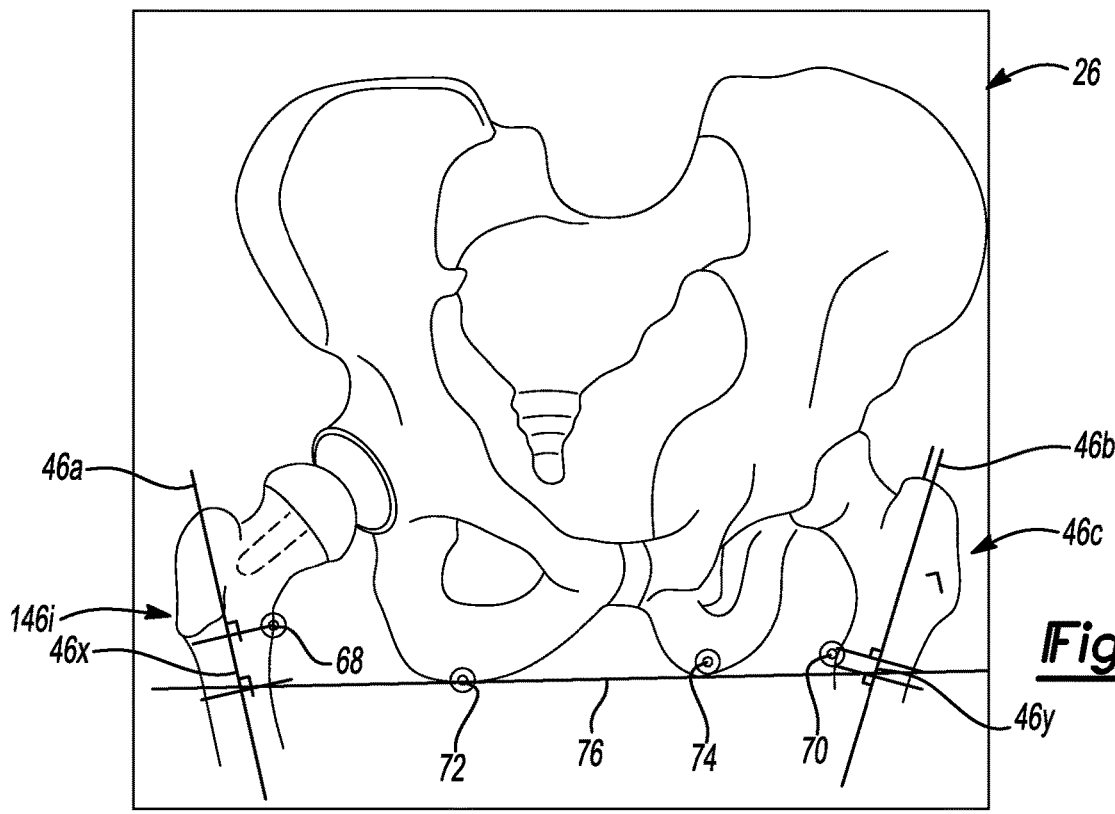
FIG. 5 is an exemplary screen shot illustrating a second geometric configuration of a subject and a prosthesis.

As a continuing example of the total hip arthroplasty, the leg length offset determination can also be made based upon the image 28 acquired of the subject 20. The leg-length offset can also be determined between the ipsilateral femur 46$i$ and the contralateral femur 46$c$, as illustrated in FIG. 5. The measurement can be made by identifying the ipsilateral lesser trochanter 68 and the contralateral lesser trochanter 70. The lesser trochanters 68-70 can define a first point on the respective femurs 46$i$-46$c$. A first axis 46$a$ of the ipsilateral femur 46$i$ and a second axis 46$b$ of the contralateral femur 46$c$ can also be identified through the respective femurs 46$i$-46$c$. A second point along the axes 46$a$ and 46$b$ of the respective femurs 46$i$ and 46$c$ can be defined as where tuberosity line 76 intersects the axes 46$a$ and 46$b$. The tuberosity line 76 is a line that extends from and between a right ischial tuberosity 72 and a left ischial tuberosity 74.

As illustrated in FIG. 5, a first distance 46$x$ is defined on the ipsilateral femur 46$i$ between a plane perpendicular to the axis 46$a$ through the ipsilateral lesser trochanter 68 and a plane that extends perpendicular to the axis 46$a$ that intersects the line 76. On the contralateral femur 46$c$, a plane perpendicular to the axis 46$b$ extends through the contralateral lesser trochanter 70 and is a second distance 46$y$ from a plane that extends perpendicular to the axis 46$b$ that intersects the line 76. As illustrated in FIG. 5, the ipsilateral distance 46$x$ is greater than the contralateral distance 46$y$. Accordingly, the leg length offset can be measured and determined in the image data. It is understood that there may not always be an offset in the distances, but they may be the same distances.

A determination of the tuberosity line 76, the planes intersecting the lesser trochanters 76, 70, and planes where the tuberosity line 76 on the respective femurs 46$i$ and 46$c$ can be made by the system 24. Additionally, or in combination therewith, the user 30 can assist in identifying the planes to determine leg length offset. It is understood that the various tuberosities, lesser trochanters, and other portions of the anatomy can be identified using various techniques including those discussed above. The system 24 can then be used to automatically identify the various anatomical portions to assist in identifying the respective axes 46$a$ and 46$b$ of the femurs 46$i$, 46$c$ and the planes extending substantially perpendicular to the respective axes 46$a$ and 46$b$. The determination of leg length offset can be used to assist in positioning the respective prostheses to create a selected leg length offset (e.g. zero) between the left and right femurs during an operative procedure to allow for a selected creation of a range of motion after the procedure.

Figure 6:
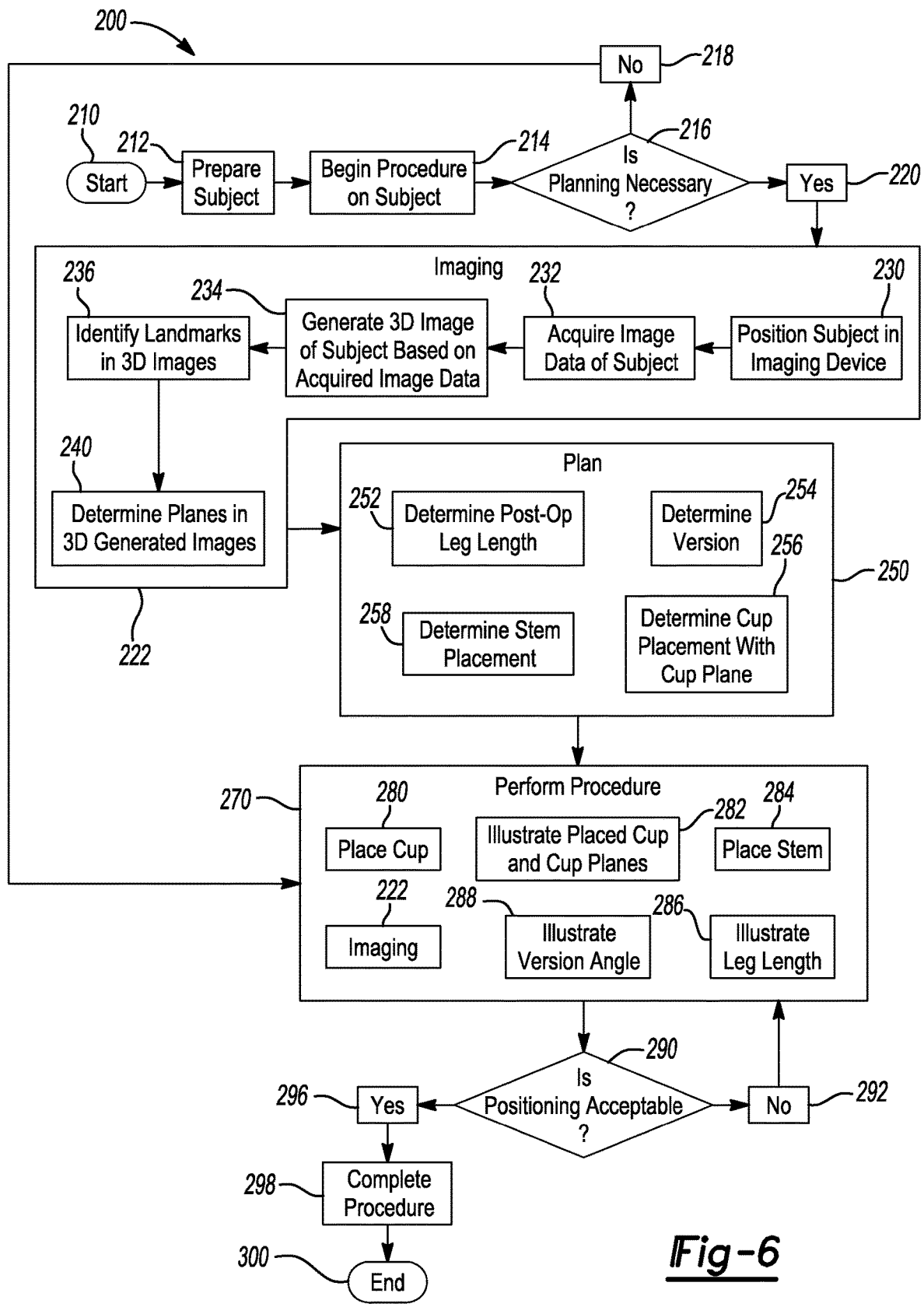
FIG. 6 is a flowchart illustrating an exemplary embodiment of using an imaging system during a procedure.

With continued reference to FIGS. 1-5 and the additional reference to FIG. 6, a flowchart 200 is illustrated. According to the flowchart 200, a procedure for using the imaging system 18, according to various embodiments, is disclosed. The process illustrated in the flowchart 200 can include the various features as discussed above, including generating or acquiring and accessing images that can be displayed on the device 26 and analyzed to illustrate various planes or orientations, as discussed above. Accordingly, the method 200, illustrated in FIG. 6, is a process that can be used to perform a procedure using the various techniques discussed above.

Accordingly, the flowchart 200 can begin at START block 210. A subject can then be prepared in block 212, such as moving a subject into the imaging system 18 to acquire images of the patient or subject 20. It is understood, however, that obtaining images of the patient 20 immediately, or prior to any step taken regarding a procedure on the subject 20 is not required. Accordingly, the method can proceed to block 214 to begin the procedure on the subject. Accordingly, preparing the subject in block 212 can include sterilizing the subject, moving the subject to an operating theater, and other steps.

After beginning the procedure on the subject 214, a decision block of whether planning is necessary 216 can be made. The decision block can follow a NO-path 218 where no planning is required or selected at the time. Alternatively, the decision block 216 can proceed through a YES-path 220 where imaging is acquired in imaging sub-routine 222 and Planning in block 250. Initially, the YES-path through block 220 will be discussed as the NO-path through block 218 proceeds by eliminating various portions of the method 200, including the planning in block 250. Accordingly, the YES-path through block 220 will be described first and an identification of where the NO-path rejoins the YES-path will be discussed herein.

After following the YES-path through block 220, the imaging sub-routine can be entered in block 222. In the imaging sub-routine 222 the patient 20 can be positioned within the imaging volume of the imaging device 18 in block 230. As illustrated in FIG. 1, the subject 20 can be positioned within the center of the O-Arm® imaging device 18 to acquire image data of the subject 20. Image data can be acquired of the subject in block 232. Generally, image data can be acquired of the subject 20 at a plurality of positions of the image device 18. As is generally understood in the art, the imaging device, such as to O-Arm® imaging device 18, has a x-ray emission and x-ray receiving portions that can move relative to the patient 18. Accordingly, a plurality of projections at various orientations can be acquired of the subject 20.

The images can be viewed individually, as two-dimensional images. In addition or alternatively a three-dimensional reconstructed image can be made based upon the two-dimensional images. Therefore, in block 234, generation three-dimensional images of the patient 20 can be made. The three-dimensional reconstruction can be made with various generally known reconstruction techniques, such as those disclosed in the patents incorporated by reference above. Generally, however, various reconstructions techniques can be used to determine the three-dimensional volume that is portrayed in the two-dimensional projections. The three-dimensional reconstruction can also be displayed on the display device 26.

The three-dimensional reconstruction can be used to identify landmarks in the image data in block 236. It is understood that the landmarks can be identified in the three-dimensional reconstruction, slice data, or the two-dimensional projections and then projected onto the three-dimensional reconstruction. The identification of the landmarks can include the techniques discussed above, such as those disclosed by Dikmen et al. The identification of the landmarks in the three-dimensional reconstruction can allow the user 30 to view the landmarks in the three-dimensional image relative to the subject 20. For example, icons representing the landmarks can be superimposed on the image data. The three-dimensional reconstruction can allow for efficient interpretation of the images displayed on the display device 26 relative to the subject 20 and for efficient use by the user 30. Accordingly, the identification of the landmarks or the icons illustrating the landmarks can be positioned on the three-dimensional reconstruction for viewing by the user 30 on the display device 26. The various landmarks can include those discussed above, such as those referenced in FIG. 2, and displayed on the display device 26. A selected number of the landmarks can be determined and displayed, such as about 2 points to about 30 points, including about 3 to about 10 points, including about 8 points. As discussed above, various planes in the image data relative to the subject 20 can also be determined, such as based on the identified landmarks, and displayed on the display device in block 240. The various landmarks and planes can be displayed as icons that are super-imposed on the image data. The icons can be superimposed on either the two-dimensional projections, slice data, or the three-dimensional reconstruction for viewing the by the user 30. The planes can assist in identifying and illustrating orientations and positions of subject 20 and/or the prosthesis or other system for use during the procedure.

An image and planning sub-routine 250 can be selectively and optionally performed based upon image data acquired of the subject 20. As discussed above, acquiring image data prior to performing a procedure or completing a procedure on the subject 20 is not required. Accordingly, imaging the patient 20 and planning of the procedure based upon image data acquired of the subject 20 is not a requirement. Nevertheless, the image and planning sub-routine 250 can exemplary be used by the user 30 to assist in identifying appropriate orientations and positions of prostheses and for determining version, leg length offset, and other anatomical positions.

The image and planning sub-routine 250 can include the various portions illustrated as blocks within the sub-routine block 250. The order of the steps in the sub-routine 250 is not required and is only discussed as having an order here for clarity of the current discussion. Thus, a selected predetermined post-operative leg length can be determined in block 252. The selected predetermined post-operative leg length in block 252 can be a leg length that is substantially the same between the left and right legs, or an appropriate differing leg length based upon anatomy of the subject 20. The version angle also be determined in block 254. The version angle can be determined based upon an anatomy of the subject and achieving selected axes and alignment of the anatomical portions of the subject 20. A determination of a cup-face plane 80*p* and placement can be made in block 256. As discussed above, the face plane 80*p* of the cup 80 can be identified and can be used to plan or determine an appropriate orientation and position of the cup 80 during a procedure.

In the exemplary total hip arthroplasty, the determination of the cup placement in block 256 and a determination of a stem-placement in block 258 can be made. The stem placement can include the length of the stem, position of the stem to achieve the version angle determined in block 254, the size of the stem, and other appropriate stem geometry and placements. It is understood, however, that various other anatomical configurations and orientations can be determined using imaging and planning procedures based upon different surgical procedures and anatomies of different subjects. For example, a shoulder replacement may not have a leg-length determination, but may have a version determination, stem replacement determination, and possibly a cup replacement determination. Accordingly, it is understood that the image and planning sub-routine in block 250 can include various procedures based upon a specific procedure performed on the subject 20.

After the planning sub-routine block 250, performing the procedure is described in block 270. It is also understood, as illustrated in the flowchart 200, if the NO-path 218 is followed after the initial determination of whether planning is necessary in block 216 that performing the procedure in sub-routine 270 can occur. Again, the specific exemplary procedure identified in block 270 includes a total hip arthroplasty. Accordingly, the discussion herein regarding a total arthroplasty is merely exemplary and other procedures can occur. It will be further understood, that the various portions of the Perform Procedure sub-routing are not required to be performed in any particular order, unless otherwise indicated herein. For example, to illustrate a placed cup in block 282 imaging in bock 222 may first occur.

In a THA performing the procedure in block 270 can begin by placing the cup in block 280. Although initial image in planning in block 250 may not occur, once various portions are places, such as the cup is placed in block 280 and/or the stem is placed in block 284, images can be acquired of the subject 20 in block 222 (here illustrated within the Perform Procedure sub-routing 270) to identify the various landmarks, planes, and angles as discussed above. Imaging according to block 222 of the subject 20 can be used to plan the procedure for the subject 20 and/or to identify and confirm a procedure based upon the user's 30 pre-determination. Thus, once the cup is placed in block 280, images can be acquired or acquired again of the subject 20 and an illustration of the placed cup and cup planes can be made in block 282. The illustrated cup and planes of the cup can include the face plane 80p and the axis 80a discussed above to illustrate the position of the cup relative to the anatomy of the subject 20, including the femur 46 and the pelvis 40.

The stem, such as in a total hip arthroplasty, can be placed in block 284. The illustration of a leg length can be made in block 286 and an illustration of a version angle in block 288 can also be made. The illustration of the leg length and the illustration of the version angle in block 288 can be based upon the images acquired of the subject 20 after positioning the cup in block 280 and positioning the stem in block 284. Accordingly, it is understood that the illustrations or collection of image data by the imaging device 18 can be performed after positioning a selected portion of the prosthetic device into the subject 20.

According to various embodiments, placing the cup in block 280 can be performed by the user 30 to initiate the procedure. After selecting the position of the acetabular cup in block 280, the user 30 can determine that positioning of the femoral prosthesis will be based thereon. Accordingly, once the cup is positioned in block 280, the user can acquire image data of the subject 20 including the pelvis 40 and the position of the cup 80 to identify the orientation of the cup relative to the pelvis and the femurs. The user 30 can use image data acquired of the subject 20 with the positioned prosthetic cup 80 to make a determination of how to achieve a selected leg length and version angle without acquiring additional image data of the subject, particularly after positioning the stem within the femur. The determination can be based upon user knowledge, patient anatomy and the like. It is understood, however, that any additional image data can be acquired, including additional post-operative image data, to further confirm placement of a prosthesis.

Accordingly, after performing the procedure and subroutine in block 270, a decision of whether the positioning is acceptable can be made in block 290. If the positioning is unacceptable, such as after determining the placement of the cup in block 280 based upon the cup face 80p and its relative position to the anatomy, including the measurement angle as illustrated in FIGS. 3A-3C, a NO-path 292 can be followed. The NO-path 292 can proceed through the performing procedure subroutine 270 including positioning and replacing the cup in block 280. For example, the cup can be reoriented in the patient 20 based upon the image data acquired of the subject 20. Additionally, the placement of the cup in block 280 can include placement of a trial prosthesis. Thus, the image data acquired of the subject can be of the trial prosthesis and a determination of a final orientation of the prosthesis can be based upon trialing the trial prosthesis after acquiring image data on the subject. Additional image data can be acquired of the patient 20 after re-orienting the prosthesis system, if selected. Additional imaging in block 222, however, may not be selected or required by the surgeon 30 and may not occur after following the NO-block 292. The geometric configurations of the patient and the prosthesis system can then be determined in the re-imaged image data.

If the determination is that the position is acceptable in block 290, then a YES-path 296 can be followed to complete the procedure in block 298 and finally END in block 300. Completing the procedure in block 298 can include various steps, such as positioning or cementing an implantable prosthetic member, closing an incision, or other appropriate steps. Additionally, the completing the procedure in block 298 can include reducing a joint, inserting fixation members (e.g., screws and cross-pins), and other procedure completing steps.

Accordingly, the method in flowchart 200 illustrates a process of acquiring image data of the subject 20 for performing a procedure on the subject 20 according to identification of orientations of the subject's anatomy and geometric configurations thereof. The anatomy includes an anatomical structure relative to the geometric configuration of the prosthesis positioned within the subject 20. Thus, the method of flowchart 200 can be used to identify and confirm positioning of the prosthesis in the subject 20 during an operative procedure by acquiring a substantially minimal amount of image data of the subject and not requiring an active navigation of surgical procedures, instruments, and prosthetic members.

Generally, a single image acquisition of the subject 20 can be made to identify various anatomical landmarks and to further identify planes of the subject and respective orientations of prosthetic members and the anatomical portions of the subject 20. The single acquisition of the image can be used to determine further steps of a procedure, such as positioning a femoral stem after positioning an acetabular prosthesis, and other determinations. The user's knowledge can be used to augment the acquired image of the subject 20 to assist in performing the procedure. The system 24, however, can assist the user 30 in substantially automatically identifying various portions of the anatomy, such as anatomical landmarks and planes of the anatomy.

The automatic determination can allow the user 30 to perform a procedure in an efficient manner without requiring the user to identify various anatomical portions and possibly incorporate error therein. It is understood, however, that the user can assist in identifying anatomical features, such as landmarks, if the user so desires and/or the system 24 has been not appropriately identified a landmark or plane based upon the user's 30 determination. Nevertheless, once a plane or landmark has been identified, the system 24 can superimpose various icons to illustrate positions of the prostheses, anatomical members, and the like for viewing by the user 30. Additionally, the user 30 can manipulate the image on the display device 26 to view a three-dimensional reconstruction from various angles to allow for a viewing angle and orientation based upon or selected by the user 30. Thus, the user 30 can efficiently perform a procedure by viewing the image data as selected by the user 30.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. Moreover, the disclosed exemplary embodiments can be generally added, interconnected, or augmented with each other, unless otherwise specified. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for using an imaging system for surgically implanting a prosthetic device into a patient, the method comprising:
    acquiring from the imaging system a first image data set comprising a pre-operative anatomical condition of the patient comprising a first three-dimensional image reconstruction of at least a portion of the patient;
    executing instructions with a processor for automatically:
        determining patient landmarks in the first three-dimensional image reconstruction,
        determining a first geometric configuration representative of at least a portion of the anatomy of the patient,
        generating a graphical representation of the determined first geometric configuration, wherein the determined first geometric configuration includes at least one of a plane, an axis, and an angle, and
        superimposing the first geometric configuration on at least the three-dimensional image reconstruction of the patient;
    determining at least one desired post-operative anatomical configuration of the patient based at least on an evaluation of the first geometric configuration;
    acquiring from the imaging device, after surgically implanting the prosthetic device into the patient, a second image data set comprising a second three-dimensional image reconstruction of the patient representing an actual post-operative anatomical condition of the patient and of the prosthetic device that has been surgically implanted into the patient;
    executing instructions with the processor or a second processor for automatically;
        determining patient landmarks in the second three-dimensional image reconstruction,
        determining a second geometric configuration representative of the anatomy of the patient and of the prosthetic device, and
        superimposing the second geometric configuration on at least the second three-dimensional image reconstruction of the patient, comprising at least one of a length, a plane, an axis, and an angle with the determined patient landmarks;
    displaying the second three-dimensional image reconstruction on the display;
    evaluating the determined second geometric configuration; and
    determining a similarity between the actual post-operative anatomical condition of the patient and the prosthetic device relative to the determined at least one desired post-operative anatomical configuration of the patient.

2. The method of claim 1, further comprising:
    operating a user input to alter a perspective of the first image data set on the display; and
    viewing the first image data set at different perspectives.

3. The method of claim 1, further comprising, prior to surgically implanting the prosthetic device into the patient, determining a third geometric configuration representative of the prosthetic device to achieve the determined at least one desired post-operative anatomical configuration of the patient, wherein the third geometric configuration comprises at least one of a length, a plane, an axis, and an angle.

4. The method of claim 3, further comprising:
    viewing on the display device the third geometric configuration superimposed on at least the first three-dimensional image reconstruction of the patient.

5. The method of claim 1, further comprising, prior to surgically implanting the prosthetic device into the patient, surgically positioning a trial prosthetic device in the patient;
    acquiring from the imaging device a third image data set comprising an actual anatomical condition of the patient and of the trial prosthetic device surgically positioned in the patient comprising:
        a third three-dimensional image reconstruction of the patient; and
        a third geometric configuration representative of the anatomy of the patient and of the trial prosthetic device superimposed on at least the third three-dimensional image reconstruction of the patient comprising at least one of a length, a plane, an axis, and an angle;
    viewing the third image data set on the display and determining whether the at least one desired post-operative anatomical configuration of the patient is achieved; and
    evaluating the third geometric configuration and determining a fourth geometric configuration representative of the prosthetic device.

6. The method of claim 5, wherein evaluating the third geometric configuration and determining a fourth geometric configuration representative of the prosthetic device comprises:
    selecting one of an operative measurement protocol, a radiographic measurement protocol, or an anatomical measurement protocol; and
    using the selected measurement protocol to determine the fourth geometric configuration.

7. The method of claim 6, wherein the first geometric configuration comprises at least one of a sagittal plane of the patient, a leg length offset of the patient, a coronal plane of the patient, an anterior pelvic plane of the patient, and a transverse plane of the patient.

8. The method of claim 7, wherein viewing the first image data set on the display comprises viewing the sagittal plane of the patient, the coronal plane of the patient, and the transverse plane of the patient.

9. The method of claim 8, wherein determining the fourth geometric configuration comprises determining a face plane of an acetabular prosthesis and an acetabular axis that is angled to the face plane and extending through an apex of the acetabular prosthesis.

10. The method of claim 9, further comprising:
    viewing an angle between the acetabular axis and at least one of the sagittal plane of the patient, the coronal plane of the patient, or the transverse plane of the patient based on the selected measurement protocol.

11. The method of claim 1, wherein the first image data set further comprises:
    a plurality of first two-dimensional image projections of at least the portion of the anatomy of the patient; and
    at least one icon representative of at least one anatomical landmark of the patient superimposed on at least the first three-dimensional image reconstruction of the patient.

12. The method of claim 11, wherein the second image data set further comprises:
    a plurality of second two-dimensional image projections of at least the portion of the anatomy of the patient; and the at least one icon representative of at least one anatomical landmark of the patient superimposed on at least the second three-dimensional image reconstruction of the patient.

13. The method of claim 5, wherein the third image data set further comprises:
a plurality of third two-dimensional image projections of the patient;
the at least one icon indicative of at least one anatomical landmark of the patient superimposed on at least the third three-dimensional image reconstruction of the patient.

14. The method of claim 1, further comprising:
tracking an instrument at least during surgically implanting the prosthetic device into the patient.

15. The method of claim 1, wherein the first geometric configuration representative of at least the portion of the anatomy of the patient comprises:
a first line extending through a right ischial tuberosity and a left ischial tuberosity;
a leg length offset including:
a right femur axis, a right lesser trochanter, a right lesser trochanter plane perpendicular to the right femur axis that intersects the right lesser trochanter, a right line plane perpendicular to the right femur axis that intersects where the first line intersects the right femur axis, a right leg distance between the right lesser trochanter plane and the right line plane along the right femur axis;
a left femur axis, a left lesser trochanter, a left lesser trochanter plane perpendicular to the left femur axis that intersects the left lesser trochanter, a left line plane perpendicular to the left femur axis that intersects where the first line intersects the left femur axis, a left distance between the left lesser trochanter plane and the left line plane along the left femur axis; and
a difference between the right distance and the left distance.

16. The method of claim 15, wherein the at least one desired post-operative anatomical configuration of the patient reduces a post-operative difference between the right distance and the left distance.

17. A method for using an imaging system for surgically implanting a prosthetic device into a patient, the method comprising:
acquiring from the imaging system a first data set comprising a pre-operative anatomical condition of the patient
operating a processor to execute instructions to automatically (i) generate a first three-dimensional image reconstruction of the patient based on the first image data set, (ii) determine patient landmarks in the first three-dimensional image reconstruction, and (iii) determine a first geometric configuration comprising at least one of a length, a plane, an axis, or an angle, wherein the first geometric configuration is representative of at least a portion of the anatomy of the patient and based on the automatically determined patient landmarks;
determining at least one desired post-operative anatomical configuration of the patient based on an evaluation of the first geometric configuration;
acquiring from the imaging device a second image data set, after the prosthetic device is implanted in the patient, comprising an actual post-operative anatomical condition of the patient and of the prosthetic device that has been surgically implanted into the patient;
operating the processor or a second processor to execute further instructions to automatically (i) generate a second three-dimensional image reconstruction of the patient, (ii) determine patient landmarks in the second three-dimensional image reconstruction, and (iii) determine a second geometric configuration comprising at least one of a length, a plane, an axis, and an angle, wherein the second geometric configuration is representative of at least the portion of the anatomy of the patient and of the prosthetic device based on the automatically determined patient landmarks;
displaying the second three-dimensional image reconstruction on the display;
evaluating the determined second geometric configuration; and
determining whether the actual post-operative anatomical condition of the patient and the prosthetic device is consistent with the determined at least one desired post-operative anatomical configuration of the patient based at least on the viewing the second three-dimensional image reconstruction on the display and the evaluating the determined second geometric configuration.

* * * * *

UNITED STATES PATENT AND TRADEMARK OFFICE
CERTIFICATE OF CORRECTION

PATENT NO. : 10,779,751 B2
APPLICATION NO. : 13/750550
DATED : September 22, 2020
INVENTOR(S) : David E. Macht Page 1 of 1

It is certified that error appears in the above-identified patent and that said Letters Patent is hereby corrected as shown below:

In the Claims

Column 15, Line 25, Claim 1, after "the", insert --first--

Signed and Sealed this
Twenty-second Day of December, 2020

Andrei Iancu
*Director of the United States Patent and Trademark Office*